United States Patent [19]

Holden et al.

[11] 4,284,556
[45] Aug. 18, 1981

[54] 7,8-AMINO, HYDROXY-1-PHENYL-2,3,4,5-TETRAHYDRO-1H-3-BENZAZEPINES

[75] Inventors: Kenneth G. Holden, Haddonfield; Carl Kaiser, Haddon Heights, both of N.J.; Joseph Weinstock, Phoenixville, Pa.

[73] Assignee: SmithKline Corporation, Philadelphia, Pa.

[21] Appl. No.: 117,181

[22] Filed: Jan. 31, 1980

[51] Int. Cl.³ .................... C07D 223/16; A61K 31/55
[52] U.S. Cl. ............................ 260/239 BB; 424/244
[58] Field of Search .................................. 260/239 BB

[56] References Cited

U.S. PATENT DOCUMENTS

| 3,314,963 | 4/1967 | Koch | 260/239 BB |
| 3,496,166 | 2/1970 | Mull et al. | 260/239 BB |
| 3,609,138 | 9/1971 | Mull et al. | 260/239 BB |
| 3,686,167 | 8/1972 | Fuimura et al. | 260/239 BB |
| 3,746,706 | 7/1973 | Krapcho | 260/239 BB |
| 4,165,372 | 8/1979 | Brush et al. | 260/239 BB X |

FOREIGN PATENT DOCUMENTS

| 555831 | 2/1967 | Switzerland | 424/244 |
| 1268243 | 3/1972 | United Kingdom | 260/239 BB |

Primary Examiner—Donald G. Daus
Assistant Examiner—W. B. Springer
Attorney, Agent, or Firm—William H. Edgerton; Richard D. Foggio; Alan D. Lourie

[57] ABSTRACT

A group of 1-phenyl-2,3,4,5-tetrahydro-1H-3-benzazepines whose structures have amino, hydroxy substituents at the 7,8-positions of the benzazepine nucleus is disclosed. Novel intermediates and routes of synthesis used for preparing them are also described. The end products have pharmacodynamic activity.

9 Claims, No Drawings

7,8-AMINO, HYDROXY-1-PHENYL-2,3,4,5-TETRAHYDRO-1H-3-BENZAZEPINES

This invention relates to a new series of 1-phenyl-2,3,4,5-tetrahydro-1H-3-benzazepines whose structures are characterized by having 7,8-amino, hydroxy substituents. These compounds have pharmacodynamic activity indicating utility as central nervous system sedatives, diuretics, antidepressants, antihypertensive agents, and especially as dopaminergic agents. As indicative of dopaminergic activity, pharmacological tests are used as described hereafter which demonstrate activity at central dopamine receptor sites indicating utility as antiparkinsonism agents or at peripheral dopamine receptor sites indicating renal dilation with resulting antihypertensive activity. Activity on the central nervous system is more pronounced with the compounds of this invention. A further important utility for these compounds is their use as chemical intermediates for preparing other pharmacodynamically active compounds as described in more detail hereafter.

PRIOR ART STATEMENT

There are in the art a number of general descriptions of the class of 1-aryl-2,3,4,5-tetrahydro-1H-3-benzazepines having one or more substituents on the benzring of the nucleus such as in U.S. Pat. Nos. 3,496,166 and 3,609,138. These patents however disclose generically only the possibility of having a dimethylamino or diethylamino substituent at an unspecified position on the benzo-fused ring of the nucleus with or without a large number of other substituents. None of the chemical methods described in the art can be used to prepare 1-phenyl-2,3,4,5-tetrahydro-1H-3-benzazepine compounds whose structures have a primary amino group substituted in the benz-ring of the 3-benzazepine nucleus. Also none of the examples in the art references described specifically any 7 or 8-amino substituted 1-phenyl-2,3,4,5-tetrahydro-1H-3-benzazepines.

U.S. Pat. No. 4,165,372 in Example 8 discloses 6-amino-7,8-dihydroxy-1-phenyl-2,3,4,5-tetrahydro-1H-3-benzazepine dihydrobromide. The chemical methods of this patent cannot be used to prepare compounds whose structures have a primary amino substituent at a ring position other than 6.

DESCRIPTION OF THE INVENTION

The compounds of this invention are represented by the following structural formula:

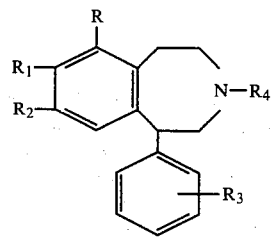

I in which:

R is hydrogen, halo such as fluoro, iodo, chloro or bromo or lower alkyl of 1–3 carbons such as methyl, ethyl or propyl;

$R_1$ and $R_2$ are hydroxy, amino, acetamido or methylsulfonamido provided that one of $R_1$ and $R_2$ is always hydroxy and that $R_1$ and $R_2$ are not both hydroxy;

$R_3$ is hydrogen, halo such as chloro, fluoro or bromo, methyl, methoxy, methylthio or hydroxy, and $R_4$ is hydrogen, allyl or methyl.

A subgeneric group of compounds of this invention are those of Formula I in which $R_1$ is amino, acetamido or methylsulfonamido and $R_2$ is hydroxy. The compounds of Formula I in which structures (1) $R_1$ is amino and $R_2$ is hydroxy or (2) $R_1$ is hydroxy and $R_2$ is amino are of particular use as chemical intermediates as described in more detail hereafter.

Also part of this invention are acid addition salts of the bases of Formula I with pharmaceutically acceptable organic and inorganic acids such as those with hydrochloric, hydrobromic, hydriodic, sulfuric, methanesulfonic, tartaric, maleic, fumaric, succinic, ethanedisulfonic or phosphoric acids.

The acid addition salts are prepared by reacting the bases in an organic solvent such as methanol or ethanol with an excess of acid as well as by other methods known to the art. It will be recognized that when one of $R_1$ or $R_2$ of the structures is a primary amine two mole equivalents of acid are necessary.

It will also be obvious to one skilled in the art that the compounds of Formula I may be present as diastereoisomers which may be resolved into d, l optical isomers. Resolution of the optical isomers may be conveniently accomplished by fractional crystallization of their salts with optically active acids from appropriate solvents. Unless otherwise specified herein or in the claims, it is intended to include all isomers, whether separated or mixtures thereof. Where isomers are separated, the desired pharmacological activity will usually predominate in one of the isomers.

The compounds of Formula I are prepared by two chemical methods. The first and most convenient is outlined in Sequence A.

SEQUENCE A

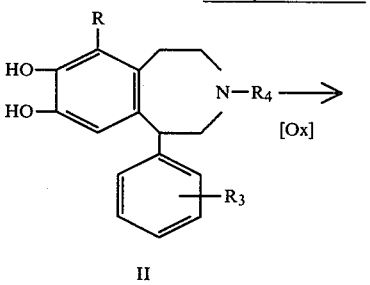

II

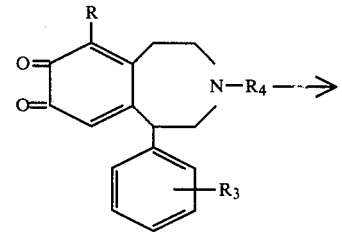

III

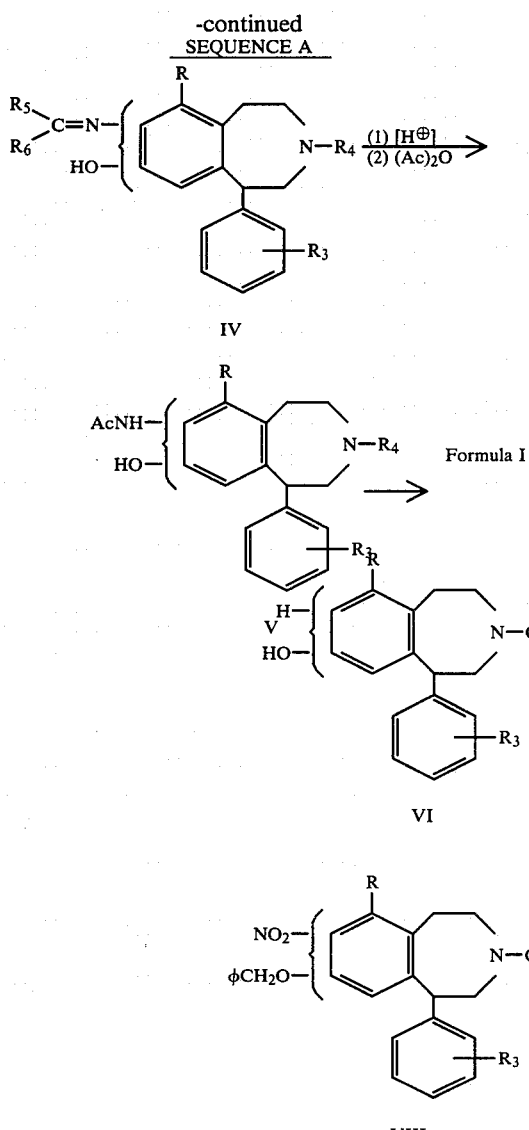

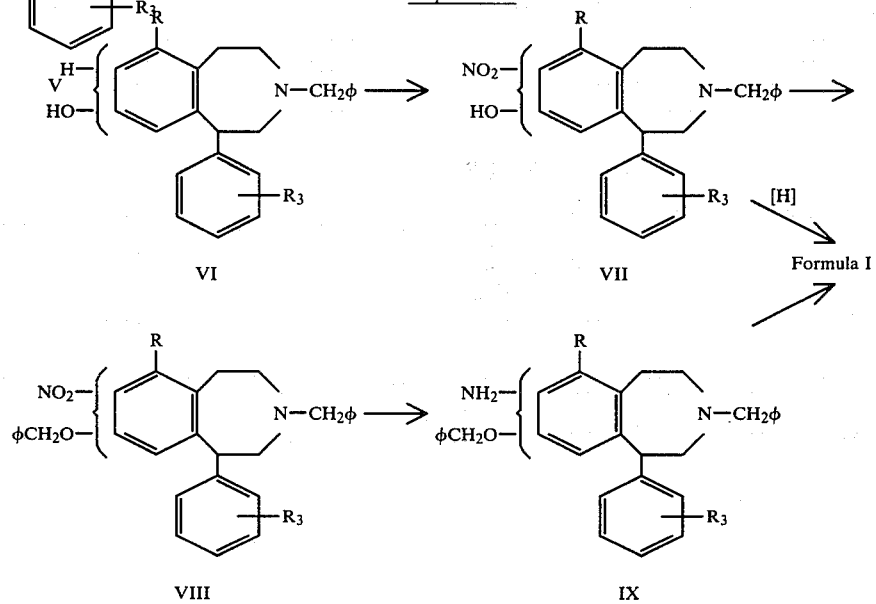

benzhydrylamine or benzylamine to give a mixture of 7,8-mono-imine or Schiff bases (IV). Most conveniently the oxidation and imine steps are carried out without isolation of the quinone. The Schiff bases are hydrolyzed with dilute acid, usually alcoholic hydrogen chloride at room temperature. The resulting 7,8-hydroxy, amino-1-phenyl-2,3,4,5-tetrahydro-1H-3-benzazepine mixture is then N-acylated using acetic anhydride in methanol followed by base hydrolysis of any acetate esters formed, and the resulting 7,8-acetamido, hydroxy compound mixture is purified by fractional crystallization or chromatography to give the individual isomeric compounds of Formula I with structures in which $R_1$ and $R_2$ are hydroxy and acetamido optionally protected at position 3. When the protective groups are removed such as by catalytic hydrogenation in case of the 3-benzyl or aqueous acid for N-acetyl moieties, the parent 1-phenylbenzazepine amino-alcohols of this invention are recovered.

In Sequence A, R and $R_3$ are as defined for Formula I, $R_4$ is allyl, methyl, or a nitrogen protecting group such as benzyl, $R_5$ represents hydrogen or phenyl optionally substituted by one or more substituents common to the art and $R_6$ represents phenyl also optionally substituted. When the outlined reactions are used to prepare compounds of Formula I in which $R_4$ is other than hydrogen such as methyl or allyl the N- protecting group is not needed.

In Sequence A, a 7,8-dihydroxy-1-phenyl-2,3,4,5-tetrahydro-1H-3-benzazepine suitably protected at the 3- or N-position of the ring by a nitrogen protecting group known to the art (II) is treated with a mild oxidizing agent such as silver oxide or 2,3-dichloro-5,6-dicyano-1,4-benzoquinone to form the 7,8-quinone (III) such as in U.S. Pat. No. 4,108,989. The quinone is treated with a slight molar excess of a suitable primary amine such as R and $R_3$ are as defined for Formula I but, of course, $R_3$ shall not be a reactive unprotected group such as hydroxy.

In the second general method of preparing the compounds of this invention illustrated in Sequence B, 1-phenyl-2,3,4,5-tetrahydro-1H-3-benzazepines with structures having a 7- or 8-hydroxy substituent and with the 3- or N-hydrogen protected are mono-nitrated, for example, in glacial acetic acid with fuming nitric acid at ambient temperature to give the 7,8-nitro, hydroxy substituted intermediates (VII). These are reduced, either as such or after O-benzylation, by controlled catalytic hydrogenation using palladium or platinum catalysts. The hydrogenation may be stopped at reduction of the nitro group or may be continued to remove the protective benzyl groups. The latter is most conveniently carried out using palladium-on-charcoal in alcoholic solution at ambient temperature and from 40–65 p.s.i.

Alternatively the 7,8-amino, hydroxy-1-phenyl-2,3,4,5-tetrahydro-1H-3-benzazepine of Formula I can be prepared by reducing the 7,8-nitro, hydroxy congeners of Formula X using low pressure catalytic hydrogenation conditions with platinum oxide as catalyst:

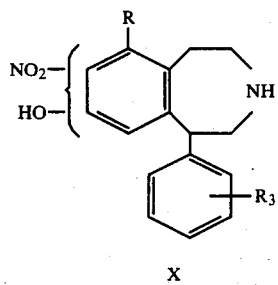

X in which R and $R_3$ are as described for Formula I.

The compounds of Formula X have weak biological activity such as a central dopaminergic effect but are most useful as chemical intermediates as disclosed hereafter.

The compounds of this invention having structures which include an N-acylated amino group at the 7 or 8 positions of the benzazepine nucleus are prepared most conveniently by the following route:

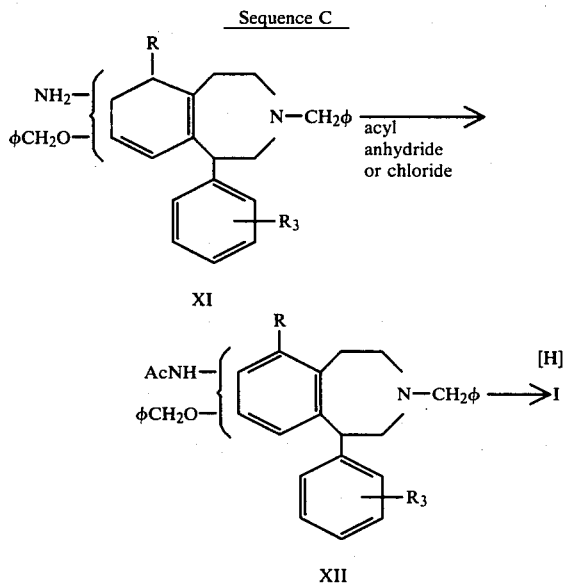

Also part of this invention are certain O- or N-benzylated intermediates of the general formula:

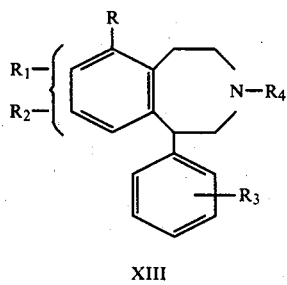

XIII in which R and $R_3$ are as defined for Formula I, $R_1$ is amino, acetamido, nitro or methylsulfonamidoyl, $R_2$ is benzyloxy or, when $R_1$ is nitro, hydroxy, and $R_4$ is benzyl, methyl, allyl or, when $R_1$ is nitro, hydrogen.

The compounds in which $R_1$ is amino are key intermediates in the preparation of other pharmacologically active compounds.

The new compounds of Formula I have pharmacodynamic activity on the central nervous and cardiovascular systems. More specifically they have been demonstrated to have activity in animal tests indicating sedative, antidepressant or dopaminergic activities. For example in the standard test procedure reported by Ungerstedt et al., in Brain Research 24, 1970, 485–493 which indicates central dopaminergic activity or more specifically antiparkinsonism activity the following results were obtained: 8-amino-7-hydroxy-1-phenyl-2,3,4,5-tetrahydro-1H-3-benzazepine dihydrochloride at 5.0 μg/rat intracaudally gave 1216±96 rotations at 2 hours and at 10.0 mg/kg intraperitoneally gave 92±64 rotations at 2 hours. 7-Hydroxy-8-methanesulfonamido-1-phenyl-2,3,4,5-tetrahydro-1H-3-benzazepine fumarate at 1.0 μg/rat intracaudally but not intraperitoneally gave 120±79 rotations at 2 hours. 8-Acetamido-7-hydroxy-1-phenyl-2,3,4,5-tetrahydro-1H-3-benzazepine hydrochloride at 2 μg/rat intracaudally gave 57±27 rotations. None of these compounds demonstrated peripheral dopaminergic activity as measured in the renal vasodilator test procedure described in U.S. Pat. No. 4,165,372, at doses of up to 6 μg/kg/min. 7-Hydroxy-8-nitro-1-phenyl-2,3,4,5-tetrahydro-1H-3-benzazepine hydrochloride gave 55±25 rotations at 10 mg/kg intraperitoneally and significant rotation intracaudally at 0.1 1.0 and 5.0 μg/rat in the central dopaminergic test.

In the anesthetized dog procedure for peripheral dopaminergic activity of U.S. Pat. No. 4,165,372, 7-amino-8-hydroxy-1-phenyl-2,3,4,5-tetrahydro-1H-3-benzazepine dihydrochloride had an $ED_{15}$ of 26 μg/kg and in the rotation test gave 314±38 rotations at 10 mg/kg intraperitoneally. 7-Acetamido-8-hydroxy-1-phenyl-2,3,4,5-tetrahydro-1H-3-benzazepine had a peripheral $ED_{15}$ of 420 μg/kg and 732 rotations at 0.1 μg/rat intracaudally in the central dopaminergic test.

7-Amino-8-hydroxy-1-phenyl-2,3,4,5-tetrahydro-1H-3-benzazepine dihydrochloride gave an $ED_{50}$ of 15.0 mg/kg intraperatoneally in preventing the ptosis caused by 1.25 mg/kg of reserpine indicating antidepressant activity equivalent to imipramine (8.35 mg/kg) at twice the dose in this standard pharmacological procedure. This compound also demonstrated sedation at an intraperitoneal dose of 37.8 mg/kg in rats. Its N-methylsulfonyl derivative demonstrated sedation at 50 mg/kg. The 7-amino compound gave significant diuretic activity in the standard phosphate-mannitol renal clearance method.

The pharmaceutical compositions containing a compound of Formula I which has biological activity are prepared in conventional dosage unit forms by incorporating the chemical compound or a pharmaceutically acceptable acid addition salt thereof, with a nontoxic pharmaceutical carrier according to accepted procedures in a nontoxic amount sufficient to produce the desired pharmacodynamic activity in a subject, animal or human. Preferably the compositions will contain the active ingredient in an active but nontoxic amount selected from about 150 mg. to about 1000 mg. of active ingredient per dosage unit but this quantity depends on the specific biological activity desired and the conditions of patient.

A wide variety of pharmaceutical forms can be employed. Thus, if a solid carrier for oral administration is used the preparation can be tableted, placed in a hard gelatin capsule in powder or pellet form, or in the form of a suppository, trouche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing pharmacodynamic activity comprises administering internally to a subject in need of such activity a compound of Formula I or a pharmaceutically acceptable acid addition salt thereof, usually combined with a pharmaceutical carrier, in a nontoxic amount sufficient to produce said activity as described above. The route of administration may be any route which effectively transports the active compound to the receptor sites which are to be affected such as orally or parenterally. Advantageously, equal doses will be administered several times such as two or three times a day with the daily dosage regimen being selected from about 300 mg. to about 2 g.

The following examples are designed solely to illustrate the preparation and use of the compounds of this invention. The temperatures are Centigrade. The doses outlined herein are in terms of the base form of the compounds of Formula I. Other variations of these examples will be obvious to those skilled in the art.

EXAMPLE 1

A mixture of 45 g. (0.134 mole) of 7,8-dihydroxy-1-phenyl-2,3,4,5-tetrahydro-1H-3-benzazepine hydrobromide, 138 g. (1 mole) of anhydrous potassium carbonate powder, 1 g. of ascorbic acid and 600 ml. of acetone was stirred after flushing with argon while 16.1 ml. (23.2 g., 0.136 mole) of benzyl bromide was added. The mixture was raised to reflux temperature, then heated at reflux for 40 minutes. The cooled mixture was filtered into excess dilute hydrochloric acid. The acid mixture was evaporated in vacuo. The residue was diluted with water and ethyl acetate then neutralized with sodium hydroxide solution adding a small quantity of ascorbic acid. Near the end point, phosphoric acid and sodium carbonate were added to buffer the mixture. At pH of 8, the organic layer was separated. The aqueous layer was extracted twice with ethyl acetate. The combined organic extracts were dried then concentrated to yield 52.9 g. of 3-benzyl-7,8-dihydroxy-1-phenyl-2,3,4,5-tetrahydro-1H-3-benzazepine as the etherate after trituration under ether, m.p. 90° (dec.).

A mixture of 16.7 g, (0.0395 mole) of the 3-benzyl compound, 36.6 g. (0.150 mole) of silver oxide, 8.7 g. (0.0475 mole) of benzhydryl amine, 11.4 g. (0.08 mole) of sodium sulfate and 150 ml. of ethyl acetate was stirred under argon at room temperature for 1.5 hours. Thin layer analysis (70% benzene-30% ethyl acetate, Rf of benzyl compound=0.53) indicated reaction was complete. The reaction mixture was filtered. The filtrate was evaporated in vacuo. The residue therefrom was dissolved in 150 ml. of methanol and treated with 50 ml. of 3 N hydrochloric acid. After 1 hour at room temperature, hydrolysis of the imines was complete (Rf=0.38 same system).

Most of the methanol was evaporated in vacuo. The residue was diluted with 200 ml. of water with 0.5 g. of ascorbic acid. After adjusting the pH to 8 using 40% sodium hydroxide solution the mixture was buffered using dilute sodium carbonate and 1 M phosphoric acid. The mixture was extracted with ethyl acetate. The combined dried extract was evaporated. The residue which was a mixture of 7,8-amino, hydroxy position isomers was dissolved in 200 ml. of methanol and 16.2 g. (0.16 mole) of acetic anhydride added in two portions 30 minutes apart. After standing overnight, an excess of 40% sodium hydroxide was added followed by brief heating on the steam bath. Most of the organic solvent was evaporated in vacuo after acidification. The residue was diluted with water then extracted with ethyl acetate with back extraction with dilute phosphoric acid. The combined aqueous phases were adjusted to pH 8–9 with sodium hydroxide and again extracted with ethyl acetate. The dried organic extracts from the pH 8–9 aqueous phase were evaporated to give a residue. The residue was dissolved in benzene and passed over a silica gel column with elution with ethyl acetate-benzene mixtures. Crystallization from ethyl acetate-hexane gave 2.01 g. (13%) of 7-acetamido-3-benzyl-8-hydroxy-1-phenyl-2,3,4,5-tetrahydro-1H-3-benzazepine (m.p. 203°–205°, Rf=0.26) and 3.41 g. (22%) of 8-acetamido-3-benzyl-7-hydroxy-1-phenyl-2,3,4,5-tetrahydro-1H-3-benzazepine (m.p. 178°–180°, Rf=0.42, benzene-ethylacetate).

A mixture of 0.50 g. (0.0013 mole) of the 8-acetamido-3-benzyl compound in 50 ml. of methanol was acidified with hydrochloric acid and hydrogenated with 1.0 g. of 10% palladium on charcoal at 60 p.s.i. After 3 hours, the mixture was flushed with argon, filtered and evaporated. The residue was taken up in 5% phosphoric acid and washed with ethyl acetate. The acid solution was adjusted to pH 8–8.5 with 40% sodium hydroxide then extracted with ethyl acetate. Drying and evaporating in vacuo gave 365 mg. (95%) of white solid, 8-acetamido-7-hydroxy-1-phenyl-2,3,4,5-tetrahydro-1H-3-benzazepine. The hydrochloride hydrate was prepared using hydrogen chloride-ethereal methanol, m.p. 181.5°.

EXAMPLE 2

A mixture of 16.3 g. (0.0385 mole) of 3-benzyl-7,8-dihydroxy-1-phenyl-2,3,4,5-tetrahydro-1H-3-benzazepine and 225 ml. of ethanol-methanol was treated with 10.7 g. (0.00462 mole) of 2,3-dichloro-5,6-dicyano-1,4-benzoquinone (DDQ) in methanol-ethanol with cooling. After stirring for 30 minutes at 0°, the precipitate is filtered, washed with ethyl acetate and then ether. The quinone is stirred with 200 ml. of tetrahydrofuran and 15 g. of 5 A° molecular sieves while a mixture of 10.6 g. (0.0578 mole) of benzhydrylamine in 30 ml. of tetrahydrofuran was added. The reaction mixture was used and worked up as in Example 1 to give 8.5 g. (57%) of 7,8-amino, hydroxy isomers. Separation of the isomers as described above but with recrystallization from ether gave 8-acetamido-3-benzyl-7-hydroxy-1-phenyl-2,3,4,5-tetrahydro-1H-3-benzazepine, m.p. 180.5°, and its 7,8-isomer, m.p. 205°–207°.

EXAMPLE 3

A mixture of 3.0 g. (0.078 mole) of 8-acetamido-3-benzyl-7-hydroxy-1-phenyl-2,3,4,5-tetrahydro-1H-3-benzazepine and 150 ml. of concentrated hydrochloric acid was heated at reflux for 2 hours. The mixture was evaporated in vacuo then again with added toluene to give 3.1 g. of yellow solid, 8-amino-3-benzyl-7-hydroxy-1-phenyl-2,3,4,5-tetrahydro-1H-3-benzazepine.

The solid was dissolved in 100 ml. of aqueous ethanol and hydrogenated with 2 g. of 10% palladium-on-charcoal. After 2 hours, the mixture was flushed, filtered and evaporated to a volume of 15 ml. Cooling overnight gave 1.8 g. (75%) of 8-amino-7-hydroxy-1-phenyl-2,3,4,5-tetrahydro-1H-3-benzazepine, m.p.>320° as the dihydrochloride salt.

EXAMPLE 4

A mixture of 4.0 g. (0.010 mole) of 7-acetamido-3-benzyl-8-hydroxy-1-phenyl-2,3,4,5-tetrahydro-1H-3-benzazepine, 0.57 ml. (0.0097 mole) of glacial acetic acid and 150 ml. of methanol-ethyl acetate was hydrogenated over 4.0 g. of 10% palladium-on-charcoal at 60 p.s.i. After 1.5 hours, the mixture was flushed with argon and filtered. The filtrate was evaporated in vacuo at 45°-50° to give a yellow-green oily residue. The residue was dissolved in water. The aqueous solution was neutralized with sodium carbonate to give 2.7 g. (87%) of white solid 7-acetamido-8-hydroxy-1-phenyl-2,3,4,5-tetrahydro-1H-3-benzazepine, m.p. 133°-143°.

EXAMPLE 5

A mixture of 3.0 g. (0.00776 mole) of 7-acetamido-3-benzyl-8-hydroxy-1-phenyl-2,3,4,5-tetrahydro-2,3,4,5-tetrahydro-1H-3-benzazepine, 0.44 g. (0.0078 mole) of acetic acid and 100 ml. of methanol-ethyl acetate (9:1) was hydrogenated over 2.0 g. of 10% palladium-on-charcoal. After working up as described in Example 4, 1.8 g. (78%) of 7-amino-8-hydroxy-1-phenyl-2,3,4,5-tetrahydro-1H-3-benzazepine dihydrochloride, m.p. 231°-235°, was isolated.

EXAMPLE 6

A mixture of 72.0 g. (0.301 mole) of 8-hydroxy-1-phenyl-2,3,4,5-tetrahydro-1H-3-benzazepine, 51.5 g. (35.8 ml, 0.301 mole) of α-bromotoluene and 45.0 g. (0.325 mole) of potassium carbonate in 1 l. of acetone was stirred at room temperature for 4 hours. The reaction mixture was filtered and the filtrate was evaporated to dryness in vacuo. The residue was treated with water and extracted with ether. The ether extracts were dried, treated with charcoal and evaporated in vacuo. The residue was taken up in benzene, then filtered to remove some insoluble material and diluted with hexane to give, on cooling, 67.3 g. (67.9%) of an off-white crystalline, m.p. 136.5°-139.5°, 3-benzyl-8-hydroxy-1-phenyl-2,3,4,5-tetrahydro-1H-3-benzazepine To a mixture of 20.0 g. (0.0607 mole) of 3-benzyl-8-hydroxy-1-phenyl-2,3,4,5-tetrahydro-1H-3-benzazepine and 500 ml. of acetic acid was added, dropwise, 3.0 ml. (4.44 g., 0.0634 mole) of 90% yellow fuming nitric acid. After stirring for 2 hours at room temperature the mixture was poured into water, neutralized with ammonia and extracted with methylene chloride. The organic extract was dried and evaporated in vacuo. The residue was chromatographed over silica gel with 25% ethyl acetatechloroform to give 11.2 g. (49%) of 3-benzyl-8-hydroxy-7-nitro-1-phenyl-2,3,4,5-tetrahydro-1H-3-benzazepine hydrochloride. This was dissolved in ethanol, acidified with ethereal hydrogen chloride and diluted with ether to give the hydrochloride salt, m.p. 264°-265° (dec.), 11.7 g. (47%).

This 3-benzyl-8-hydroxy-7-nitro-1-phenyl-2,3,4,5-tetrahydro-1H-3-benzazepine hydrochloride (7.7 g., 0.019 mole) was hydrogenated in 100 ml. of methanol over 2 g. of 10% palladium-on-charcoal over 2 hours. The reaction mixture was flushed with argon, filtered. The filtrate was acidified with ethereal hydrogen chloride (Congo Red). Concentration of the filtrate to 50 ml. followed by dilution with ether and cooling gave 3.8 g. (63%) of a tan crystalline solid, m.p. 227°-229° (dec.), 7-amino-8-hydroxy-1-phenyl-2,3,4,5-tetrahydro-1H-3-benzazepine dihydrochloride.

EXAMPLE 7

Three milliliters (0.0634 mole) of 90% fuming nitric acid was added dropwise to a solution of 20.0 g. (0.0607 mole) of 3-benzyl-8-hydroxy-1-phenyl-2,3,4,5-tetrahydro-1H-3-benzazepine prepared as described for its isomer above, m.p. 136.5°-139.5°, in 500 ml. of glacial acetic acid. After 2 hours, the mixture was poured on ice and neutralized with ammonia then extracted with methylene chloride. The dried extract was evaporated to 500 ml. Chromatography over silica with ethyl acetate-chloroform (1:4) gave 11.15 g. (49%) of oily 3-benzyl-8-hydroxy-7-nitro-1-phenyl-2,3,4,5-tetrahydro-1H-3-benzazepine.

EXAMPLE 8

A mixture of 1.8 g. of 3-benzyl-7-hydroxy-8-nitro-1-phenyl-2,3,4,5-tetrahydro-1H-3-benzazepine hydrochloride was converted to crude base which was dissolved in 50 ml. of benzene and added to a mixture of 0.75 g. of cyanogen bromide in benzene at 50°-55°. After 35 hours a small amount of unreacted starting material was detected. Additional cyanogen bromide (0.2 g) was added then heat at 55° overnight was applied. The mixture was stripped. A mixture of 25 ml. of acetic acid and 40 ml. of 3 N hydrochloric acid was added to the residue. The mixture was heated at reflux with stirring overnight. After filtering hot, the filtrate was evaporated in vacuo to a yellow solid. After recrystallization from methanol-ethyl acetate, 1 g. (85%) of 7-hydroxy-8-nitro-1-phenyl-2,3,4,5-tetrahydro-1H-3-benzazepinehydrochloride was recovered as the monohydrate.

Using the same reaction conditions and work up as above, 1.4 g. (0.0132 mole) of cyanogen bromide in benzene (25 ml) and 4.12 g. (0.011 mole) of 3-benzyl-8-hydroxy-7-nitro-1-phenyl-2,3,4,5-tetrahydro-1H-3-benzazepine was reacted at 50°-55° to give 8-hydroxy-7-nitro-1-phenyl-2,3,4,5-tetrahydro-1H-3-benzazepine hydrochloride, m.p. 252°-255° (dec.).

EXAMPLE 9

A mixture of 7.0 g. (0.0180 mole) of 8-acetamido-3-benzyl-7-hydroxy-1-phenyl-2,3,4,5-tetrahydro-1H-3-benzazepine, 2.3 g. (0.0180 mole) of benzyl chloride, 0.725 g. (0.0180 mole) of 40% sodium hydroxide and 450 ml. of aqueous acetic acid was heated at reflux overnight. The bulk of the acetone was evaporated in vacuo. The residue was quenched with water then extracted with ethyl acetate. The extracts were washed with alkali, dried and evaporated to give 5.6 g. (65%) of 8-acetamido-3-benzyl-7-benzyloxy-1-phenyl-2,3,4,5-tetrahydro-1H-3-benzazepine (Rf=0.53).

A mixture of 4.4 g. (0.0092 mole) of the dibenzyl compound and 110 ml. of 2% hydrochloric acid was heated at 95°-100° for several hours. The mixture was made basic with 10% sodium hydroxide then extracted with ether. After drying, charcoaling and evaporating the extract gave, after alumina chromatography, 2.5 g. (62.5%) of 8-amino-3-benzyl-7-benzyloxy-1-phenyl-2,3,4,5-tetrahydro-1H-3-benzazepine, a key intermediate, m.p. 119°–120°.

EXAMPLE 10

A mixture of 6.2 g. (0.0143 mole) of the 8-amino compound from Example 9, 1.72 g. (0.0150 mole) of methanesulfonyl chloride, 30 ml. of triethylamine and 200 ml. of benzene was stirred at room temperature overnight. Assay of the mixture indicated incomplete reaction. An additional 0.6 ml. (0.0075 mole) of sulfonyl chloride was added and the reaction continued until completion. The reaction mixture was washed with alkali, dried and evaporated. The residual oil (8.1 g.) was dissolved in methane and seeded to give crystalline 3-benzyl-7-benzyloxy-8-methylsulfonamido-1-phenyl-2,3,4,5-tetrahydro-1H-3-benzazepine, m.p. 136°–138°.

This intermediate (3.55 g., 0.00693 mole) was dissolved in methanol-ethanol (1:1) and hydrogenated over 10% palladium-on-charcoal in an acid medium. The mixture was flushed with argon, filtered and the filtrate evaporated. The residue was taken up in water and neutralized with sodium carbonate. The resulting solid was taken up in methanol. The filtrate was reacted with an excess of fumaric acid in methanol. After filtration ether is added to induce crystallization of 1.0 g. of 7-hydroxy-8-methylsulfonamido-1-phenyl-2,3,4,5-tetrahydro-1H-3-benzazepine hemifumarate hydrate, m.p. 178°–182° (dec.).

EXAMPLE 11

A mixture of 2 g. of 3-benzyl-6-chloro-7,8-dihydroxy-1-phenyl-2,3,4,5-tetrahydro-1H-3-benzazepine hydrobromide (prepared as described above from starting material disclosed in U.S. Pat. No. 4,108,989), 1.3 g. of sodium oxide, 3.6 g. of silver sulfate, 1.0 g. of benzylamine and 75 ml. of ethyl acetate is stirred in an inert atmosphere for several hours. Working up and further reaction as described above in Example 1 gives the 7,8-isomeric mixture of benzylimino compounds of Formula IV in which R is chloro and $R_3$ is hydrogen, the two 7,8-acetamido, hydroxy-3-benzyl-6-chloro-1-phenyl-2,3,4,5-tetrahydro-1H-3-benzazepines and finally, after hydrogenolysis, 7-acetamido-6-chloro-8-hydroxy-1-phenyl-2,3,4,5-tetrahydro-1H-3-benzazepine and 8-acetamido-6-chloro-7-hydroxy-1-phenyl-2,3,4,5-tetrahydro-1H-3-benzazepine.

EXAMPLE 12

Repeating the reaction sequence and isolation procedures of Example 1 but using
(a) 6-fluoro-7,8-dihydroxy-1-phenyl-2,3,4,5-tetrahydro-1H-3-benzazepine (U.S. Pat. No. 4,108,989),
(b) 6-propyl-7,8-dihydroxy-1-phenyl-2,3,4,5-tetrahydro-1H-3-benzazepine (U.S. Pat. No. 4,165,372),
(c) 7,8-dihydroxy-1-(3-trifluoromethylphenyl)-2,3,4,5-tetrahydro-1H-3-benzazepine (U.S. Pat. No. 4,171,359),
(d) 6-chloro-7,8-dihydroxy-1-(3-methylphenyl)-2,3,4,5-tetrahydro-1H-3-benzazepine (U.S. Pat. No. 4,171,359),
(e) 6-chloro-7,8-dihydroxy-1-(4-methoxyphenyl)-2,3,4,5-tetrahydro-1H-3-benzazepine,
(f) 6-chloro-7,8-dihydroxy-3-methyl-1-phenyl-2,3,4,5-tetrahydro-1H-3-benzazepine (U.S. Pat. No. 4,160,765) which does not require N-protection and
(g) 3,6-dimethyl-7,8-dihydroxy-1-phenyl-2,3,4,5-tetrahydro-1H-3-benzazepine hydrochloride (U.S. Pat. No. 4,165,372) which does not require N-protection, give compounds of this invention as follows:
(a)
8-acetamido-6-fluoro-7-hydroxy-1-phenyl-2,3,4,5-tetrahydro-1H-3-benzazepine
8-amino-6-fluoro-7-hydroxy-1-phenyl-2,3,4,5-tetrahydro-1H-3-benzazepine
7-acetamido-6-fluoro-8-hydroxy-1-phenyl-2,3,4,5-tetrahydro-1H-3-benzazepine and
7-amino-6-fluoro-8-hydroxy-1-phenyl-2,3,4,5-tetrahydro-1H-3-benzazepine
(b)
8-acetamido-6-propyl-7-hydroxy-1-phenyl-2,3,4,5-tetrahydro-1H-3-benzazepine
8-amino-6-propyl-7-hydroxy-1-phenyl-2,3,4,5-tetrahydro-1H-3-benzazepine
7-acetamido-6-propyl-8-hydroxy-1-phenyl-2,3,4,5-tetrahydro-1H-3-benzazepine and
7-amino-6-propyl-8-hydroxy-1-phenyl-2,3,4,5-tetrahydro-1H-3-benzazepine
(c)
8-acetamido-7-hydroxy-1-(3-trifluoromethylphenyl)-2,3,4,5-tetrahydro-1H-3-benzazepine and
7-acetamido-8-hydroxy-1-(3-trifluoromethylphenyl)-2,3,4,5-tetrahydro-1H-3-benzazepine
(d)
8-acetamido-6-chloro-7-hydroxy-1-(3-methylphenyl)-2,3,4,5-tetrahydro-1H-3-benzazepine
8-amino-6-chloro-7-hydroxy-1-(3-methylphenyl)-2,3,4,5-tetrahydro-1H-3-benzazepine
7-acetamido-6-chloro-8-hydroxy-1-(3-methylphenyl)-2,3,4,5-tetrahydro-1H-3-benzazepine and
7-amino-6-chloro-8-hydroxy-1-(3-methylphenyl)-2,3,4,5-tetrahydro-1H-3-benzazepine
(e)
8-acetamido-6-chloro-7-hydroxy-1-(4-methoxyphenyl)-2,3,4,5-tetrahydro-1H-3-benzazepine
8-amino-6-chloro-7-hydroxy-1-(4-methoxyphenyl)-2,3,4,5-tetrahydro-1H-3-benzazepine
7-acetamido-6-chloro-8-hydroxy-1-(4-methoxyphenyl)-2,3,4,5-tetrahydro-1H-3-benzazepine
7-amino-6-chloro-8-hydroxy-1-(4-methoxyphenyl)-2,3,4,5-tetrahydro-1H-3-benzazepine, and, after reacting the two acetamido products with 48% hydrobromic acid as described in U.S. Pat. No. 4,171,359,
8-amino-6-chloro-7-hydroxy-1-(4-hydroxyphenyl)-2,3,4,5-tetrahydro-1H-3-benzazepine and its dihydrobromide salt
7-amino-6-chloro-8-hydroxy-1-(4-hydroxyphenyl)-2,3,4,5-tetrahydro-1H-3-benzazepine and its dihydrobromide salt, as well as after N-allylation of the 7 or 8-acetamido compound followed by hydrobromic acid treatment using methods described in U.S. Pat. No. 4,171,359.
3-allyl-8-amino-6-chloro-7-hydroxy-1-(4-hydroxyphenyl)-2,3,4,5-tetrahydro-1H-3-benzazepine and its dihydrochloride salt or its 7,8 isomer
(f)
8-acetamido-6-chloro-7-hydroxy-3-methyl-1-phenyl-2,3,4,5-tetrahydro-1H-3-benzazepine
7-acetamido-6-chloro-8-hydroxy-3-methyl-1-phenyl-2,3,4,5-tetrahydro-1H-3-benzazepine (g)
8-amino-3,6-dimethyl-7-hydroxy-1-phenyl-2,3,4,5-tetrahydro-1H-3-benzazepine
7-amino-3,6-dimethyl-8-hydroxy-1-phenyl-2,3,4,5-tetrahydro-1H-3-benzazepine.

These compounds are conveniently isolated as the base or one of its hydrohalide or methanesulfonate salts.

What is claimed is:

1. A compound of the formula:

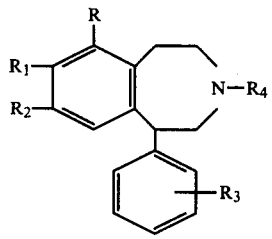

in which:

R is hydrogen, halo or lower alkyl of 1–3 carbons;
$R_1$ and $R_2$ are hydroxy, amino, acetamido or methylsulfonamido with the proviso that one of $R_1$ and $R_2$ is always hydroxy and $R_1$ and $R_2$ are not both hydroxy;
$R_3$ is hydrogen, halo, methyl, methoxy, methylthio or hydroxy; and
$R_4$ is hydrogen, allyl or methyl; together with pharmaceutically acceptable, acid addition salts thereof.

2. The compound of claim 1 in which $R_2$ is hydroxy.

3. The compound of claim 1 in which $R_2$ is hydroxy and $R_1$ is amino.

4. The compound of claim 1 being 7-amino-8-hydroxy-1-phenyl-2,3,4,5-tetrahydro-1H-3-benzazepine or one of its pharmaceutically acceptable acid addition salts.

5. A compound of claim 1 being 3-allyl-7-amino-6-chloro-8-hydroxy-1-(4-hydroxyphenyl)-2,3,4,5-tetrahydro-1H-3-benzazepine or one of its pharmaceutically acceptable acid addition salts.

6. The compound of claim 1 being 7-amino-6-chloro-8-hydroxy-1-(4-hydroxyphenyl)-2,3,4,5-tetrahydro-1H-3-benzazepine or one of its pharmaceutically acceptable acid addition salts.

7. The compound of claim 1 being 7-hydroxy-8-methylsulfonamido-1-phenyl-2,3,4,5-tetrahydro-1H-3-benzazepine.

8. The compound of claim 1 being 8-amino-7-hydroxy-1-phenyl-2,3,4,5-tetrahydro-1H-3-benzazepine dihydrochloride.

9. The compound of claim 1 being 8-acetamido-7-hydroxy-1-phenyl-2,3,4,5-tetrahydro-1H-3-benzazepine.

* * * * *